United States Patent
Rothfritz et al.

[11] Patent Number: 6,002,482
[45] Date of Patent: Dec. 14, 1999

[54] DISPOSABLE CALIBRATION DEVICE

[75] Inventors: Robert Rothfritz, Marietta; Scott Kerr, Stone Mountain; Glenn Steven Arche; Scott Kellogg, both of Duluth; Gregory J. Newman, Atlanta; Mark A. Samuels, Norcross; Richard Lachlan Fowler, Lawrenceville; Shabbir Bambot, Suwanee, all of Ga.

[73] Assignee: Spectrx, Inc., Norcross, Ga.

[21] Appl. No.: 09/124,090

[22] Filed: Jul. 29, 1998

Related U.S. Application Data

[63] Continuation-in-part of application No. 09/054,490, Apr. 3, 1998, Pat. No. 5,924,981, which is a continuation-in-part of application No. 08/904,766, Aug. 1, 1997, which is a continuation-in-part of application No. 08/621,182, Mar. 21, 1996, abandoned, which is a continuation-in-part of application No. 08/587,949, Jan. 17, 1996, Pat. No. 5,860,421.

[51] Int. Cl.$^6$ .................................................. G01B 9/02
[52] U.S. Cl. ........................................ 356/351; 600/306
[58] Field of Search .................. 378/44, 48, 98; 356/351, 357, 346; 346/10, 19; 600/306, 315

[56] References Cited

U.S. PATENT DOCUMENTS

| | | | |
|---|---|---|---|
| 3,677,652 | 7/1972 | Little | 356/183 |
| 4,029,085 | 6/1977 | Dewitt et al. | 128/2 |
| 4,177,798 | 12/1979 | Leveque et al. | |
| 4,241,738 | 12/1980 | Lubbers et al. | |
| 4,267,844 | 5/1981 | Yamanishi | 128/633 |
| 4,322,164 | 3/1982 | Shaw et al. | 356/243 |
| 4,344,438 | 8/1982 | Schultz | |
| 4,360,270 | 11/1982 | Jeck | 356/243 |
| 4,362,935 | 12/1982 | Clark, III | 378/48 |
| 4,423,736 | 1/1984 | DeWitt et al. | |
| 4,495,413 | 1/1985 | Lerche et al. | 250/252.1 |
| 4,499,375 | 2/1985 | Jaszczak | 250/252.1 |
| 4,500,782 | 2/1985 | Allemann et al. | 250/291 |
| 4,642,422 | 2/1987 | Garwin et al. | 178/18 |
| 4,700,708 | 10/1987 | New et al. | 128/633 |

(List continued on next page.)

FOREIGN PATENT DOCUMENTS 747 002 A1  11/1996  European Pat. Off. .......... A61B 5/00

*Primary Examiner*—George Manuel
*Attorney, Agent, or Firm*—Fleshner & Kim

[57] ABSTRACT

A combined infection shield and calibration or reference target for use with a measuring instrument includes a removable calibration/reference layer. The removable calibration/reference layer has predetermined optical characteristics that can be utilized to calibrate or reference the instrument. The calibration/reference layer may have predetermined reflectance or scattering properties, a predetermined transmissivity to light, or it may have predetermined fluorescence properties. When the calibration/reference layer is removed from the remaining portions of the device, the portion of the calibration/reference layer having the predetermined optical characteristics is irrevocably altered such that the calibration/reference layer cannot be reused. The combined infection shield and target may be attached to a shield holder, which in turn is attached to an instrument. Alternatively, the infection shield and target may be attached directly to an instrument.

61 Claims, 8 Drawing Sheets

U.S. PATENT DOCUMENTS

| | | | |
|---|---|---|---|
| 4,744,656 | 5/1988 | Moran et al. | 356/243 |
| 4,768,516 | 9/1988 | Stoddart et al. . | |
| 4,770,179 | 9/1988 | New et al. | 128/633 |
| 4,790,324 | 12/1988 | O'Hara et al. . | |
| 4,796,633 | 1/1989 | Zwirkoski | 128/634 |
| 4,847,493 | 7/1989 | Sodal et al. | 250/252.1 |
| 4,867,557 | 9/1989 | Takatani et al. . | |
| 4,868,126 | 9/1989 | Schwartz | 436/10 |
| 4,894,547 | 1/1990 | Lefell et al. . | |
| 4,911,559 | 3/1990 | Meyst et al. . | |
| 4,914,720 | 4/1990 | Knodle et al. | 250/343 |
| 4,975,581 | 12/1990 | Robinson et al. | 250/339 |
| 4,981,355 | 1/1991 | Higgins | 356/243 |
| 5,030,986 | 7/1991 | Dwyer et al. | 355/20 |
| 5,088,834 | 2/1992 | Howe et al. . | |
| 5,119,819 | 6/1992 | Thomas et al. . | |
| 5,146,091 | 9/1992 | Knudson . | |
| 5,169,235 | 12/1992 | Tominaga et al. . | |
| 5,311,273 | 5/1994 | Tank et al. | 356/43 |
| 5,337,289 | 8/1994 | Fashing et al. | 367/140 |
| 5,349,961 | 9/1994 | Stoddart et al. . | |
| 5,353,790 | 10/1994 | Jacques et al. | 128/633 |
| 5,355,880 | 10/1994 | Thomas et al. . | |
| 5,360,004 | 11/1994 | Purdy et al. . | |
| 5,365,925 | 11/1994 | Lee | 128/634 |
| 5,371,358 | 12/1994 | Chang et al. | 250/226 |
| 5,383,452 | 1/1995 | Buchert . | |
| 5,411,032 | 5/1995 | Esseff et al. . | |
| 5,416,816 | 5/1995 | Wenstrup et al. | 378/18 |
| 5,435,309 | 7/1995 | Thomas et al. . | |
| 5,458,140 | 10/1995 | Eppstein et al. . | |
| 5,487,607 | 1/1996 | Makita et al. . | |
| 5,557,399 | 9/1996 | De Groot | 356/357 |
| 5,792,049 | 8/1998 | Eppstein et al. | 600/306 |

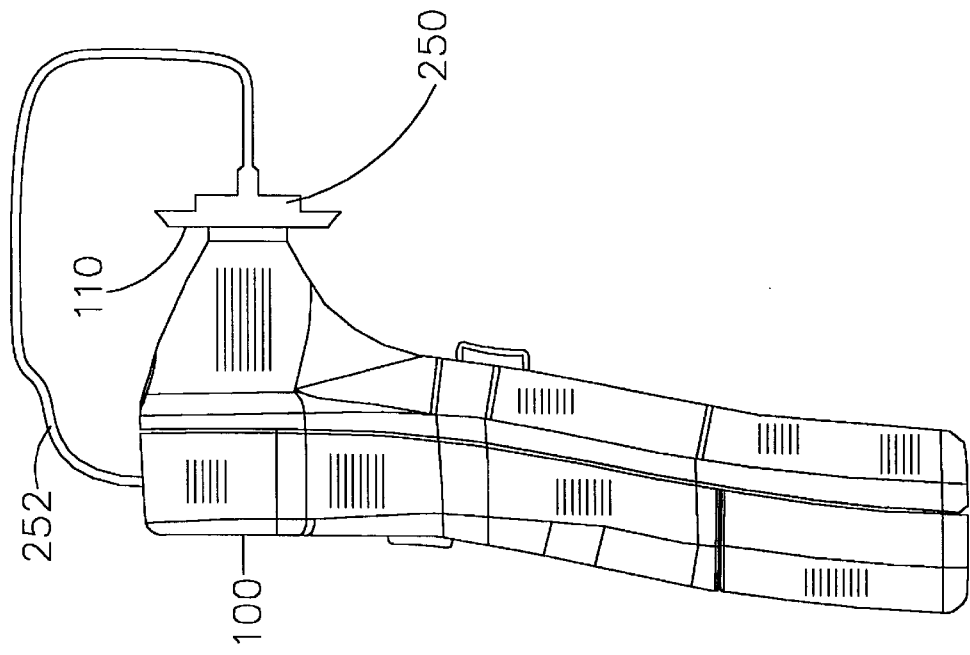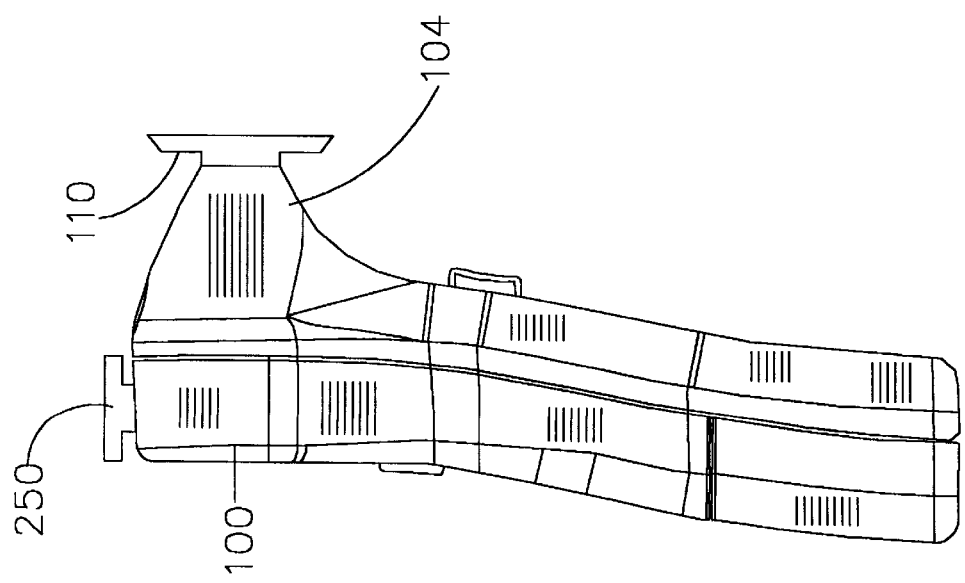

DISPOSABLE CALIBRATION DEVICE

This application is a continuation-in-part of U.S. patent application Ser. No. 09/054,490, filed Apr. 3, 1998 now U.S. Pat. No. 5,924,984; which in turn is a continuation-in-part of U.S. patent application Ser. No. 08/904,766, filed Aug. 1, 1997; which in turn is a continuation-in-part of U.S. patent application Ser. No. 08/621,182, filed Mar. 21, 1996 now abandoned; which in turn is a continuation-in-part of U.S. patent application Ser. No. 08/587,949, filed Jan. 17, 1996. The contents of all four parent applications are hereby incorporated by reference.

BACKGROUND OF THE INVENTION

1. Field of the Invention

The invention relates to a device for calibrating a measuring instrument or serving as a reference target.

2. Background of the Related Art

There are a variety of measuring instruments that utilize electromagnetic radiation to detect physical characteristics or conditions of a material. Such instruments may be used to detect colors or spectroscopic characteristics of objects, or to determine a characteristic of an object. Such an instrument may also be used by medical personnel to diagnose a condition of a patient.

Typically, the instrument will emit radiation at one or more wavelengths, and the emitted radiation is directed toward a target object, or target tissue on a patient. Reflected, transmitted, scattered or emitted radiation that interacts with the target object or tissue, or possibly fluorescent radiation generated by the target object or tissue in response to the emitted radiation, is then detected by the instrument and analyzed to determine characteristics of the target object or tissue, or to determine a condition of the patient.

An example of such an instrument is shown in FIG. 1. The instrument 100 includes a trigger 102 for activating the device. When activated, the device emits radiation at one or more wavelengths from a nose portion 104. Radiation that is reflected, transmitted, scattered or emitted from the target object or patient is then collected by the nose portion 104 and analyzed by a detector of the instrument to determine a characteristic of the target object, or a condition of the patient. The instrument could also be configured such that it receives and analyzes radiation that is naturally emitted from the tissue or object.

Instruments like the one shown in FIG. 1 may require periodic calibration to maintain their accuracy. Over time, various characteristics of the instrument, including the amplitude of the output radiation and the spectral distribution of the output radiation, as well as the total radiation power output, can vary due to environmental conditions, or simple aging of the radiation emitting elements and other elements in the instrument. In addition, a detector of the instrument can have differing sensitivities depending upon environmental conditions or the age of the detector. For instance, a change in temperature of only a few degrees can significantly affect the sensitivity of a radiation detector. For these reasons, the measuring instrument may require a calibration or reference reading prior to taking an actual measurement.

In a calibration operation, the instrument is aimed at a calibration target having known optical properties and radiation is directed toward the target. Radiation is then reflected, transmitted, scattered or emitted by the calibration target and detected by a detector of the instrument. Because the calibration target has known optical properties, the amount and distribution of radiation reflected, transmitted, scattered or emitted by the calibration target and received back in the instrument provides an indication of the radiation directed toward the target. A calibration operation allows a baseline measurement to be taken in order to determine the qualitative end quantitative performance of the light source, detector and other instrument components in order to ensure that the instrument will deliver accurate results.

In a reference operation, the instrument is aimed at a target having known optical properties and radiation is directed toward the target. A predetermined amount of radiation generated by the instrument is reflected, transmitted or scattered by the target, or the radiation causes the target to emit radiation. This reflected, transmitted, scattered or emitted radiation is detected by the detector of the instrument. The results of detection operation can then be used as a standard or reference against which a target object or patient measurement is judged. A reference operation is typically conducted at the point of use. A target object or patient reading could then be derived by determining a difference or ratio between a target object or patient detection operation, and a detection operation conducted on a reference target. Because the optical properties of the reference target are known, variations in light output or detector sensitivity can be accounted for by use of the reference target. This ensures that the instrument continues to deliver accurate results.

SUMMARY OF THE INVENTION

The invention is a device and method that can be used to calibrate or reference a measuring instrument for purposes of taking a measurement.

A calibration or reference device embodying the invention may include a fluorescent portion that produces fluorescent radiation in response to an excitation radiation. The excitation radiation may come from the instrument itself or from an external source.

A calibration or reference device embodying the invention may also be at least partially transmissive to radiation, so that radiation transmitted through the device can be used to conduct a calibration or reference operation. The optical properties of the transmissive calibration/reference device are controlled so that a predetermined amount of radiation is allowed to pass through the target. This type of device could be used with a radiation source in the instrument itself, or with an external source of radiation.

A calibration or reference device embodying the invention may include a shield to prevent contamination or infection of the measured article. In some embodiments, the device may comprise both an infection/contamination shield and a calibration or reference target with known optical properties integrated into a single unitary element.

A device embodying the invention is configured to be attached to the operative end of a measuring instrument. Once attached, the instrument may perform one or more measurement cycles using a calibration or reference target of the device having known optical properties. After a calibration/reference operation has been successfully performed, the portion of the target relevant to the calibration/reference is removed and the instrument is used to perform an object or patient measurement. If the target device incorporates a contamination/infection shield, the shield may remain attached to the instrument to prevent contamination or infection of the measured object/patient.

In a preferred embodiment, the device is configured such that removal of the target irrevocably destroys the portion of the target relevant to the calibration/reference operation, thus precluding another use of the target. As explained more fully below, when such a device embodying the invention is used with a medical instrument which is configured to perform only a single patient reading after each calibration/reference operation, such use can help to ensure that patients are not contaminated or infected, and that no cross-contamination between patients is possible.

Methods embodying the invention could make use of reflective, transmissive or fluorescent calibration/reference devices described above.

In a method embodying the invention that makes use of a fluorescent calibration target, excitation radiation would be applied to the fluorescent portion of the target, and fluorescent radiation generated by the target would be used to perform a calibration or reference operation. In such a method, the step of detecting the fluorescent radiation generated by the target could comprise determining time characteristics of the fluorescent emissions through a burst and monitor method, a phase shift method, or a fluorescence depolarization method.

In methods embodying the invention that make use of a transmissive calibration/reference device, radiation could be generated by the measuring instrument, or an external light source, and the excitation radiation would be applied to the transmissive portion of the calibration/reference device. Radiation passing through the transmissive portion is then detected by the measuring instrument and used to conduct a calibration/reference operation.

Additional advantages, objects, and features of the invention will be set forth in part in the description which follows, and in part will become apparent to those having ordinary skill in the art upon examination of the following, or may be learned from practice of the invention. The objects and advantages of the invention may be realized and attained as particularly pointed out in the appended claims.

BRIEF DESCRIPTION OF THE DRAWINGS

Preferred embodiments of the invention will be described in conjunction with the following drawing figures, wherein like reference numerals refer to like elements, and wherein:

FIG. 20A is a diagram of a measuring instrument embodying the invention, and

FIG. 20B is a diagram showing a measuring instrument embodying the invention conduction a calibration/reference operation with a transmissive calibration target.

DETAILED DESCRIPTION OF PREFERRED EMBODIMENTS

The terms "calibration target" and "reference target" are used interchangeably in the following text to refer to a target having known optical properties. The invention is applicable to both calibration targets and reference targets, and use of either term should not be construed as limiting. Also, measuring instruments that utilize the methods and calibration/reference targets embodying the invention make use of electromagnetic radiation. The terms electromagnetic radiation, radiation and light are intended to be equivalent terms, all of which refer to electromagnetic radiation.

A calibration/reference device embodying the invention may be comprised of several parts. The first part is simply a device for anchoring a contamination/infection shield and a calibration/reference target to a measuring instrument. If the instrument is like the one shown in FIG. 1, a shield holder 110, as shown in FIG. 2, can be used to attach an infection/contamination shield and a calibration/reference target to the nose portion 104 of the instrument 100.

Figure 2:
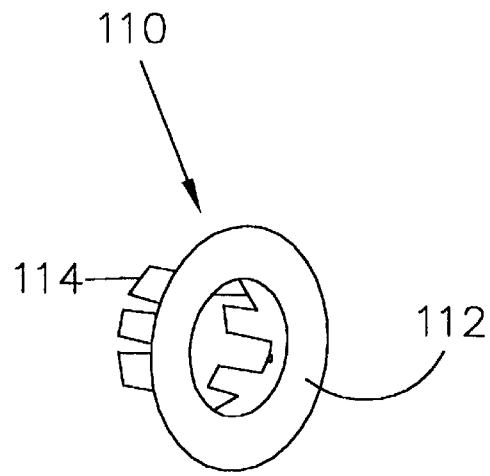
FIG. 2 is a perspective view of a portion of a calibration/reference device embodying the invention.
Figure 3:
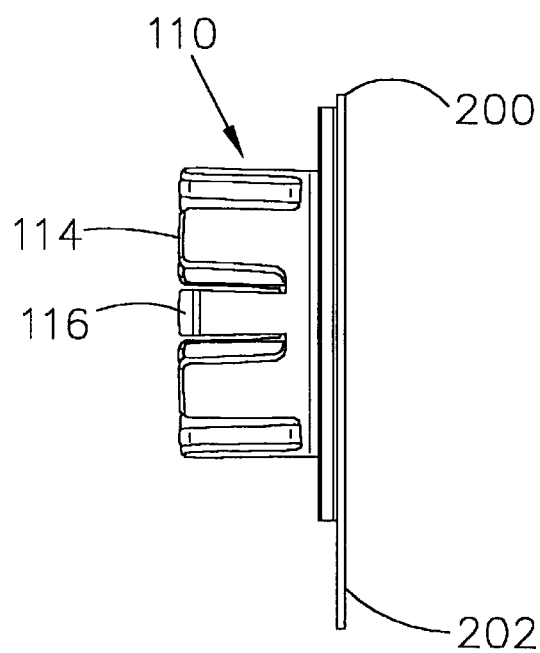
FIG. 3 is a side view of a calibration/reference device embodying the invention.
Figure 4:
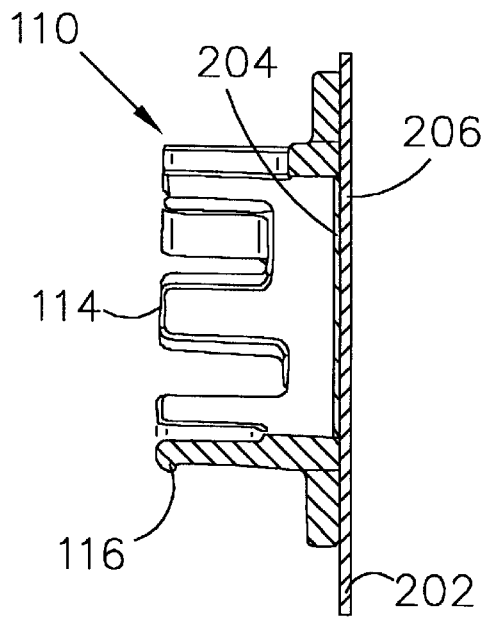
FIG. 4 is a sectional view of a second calibration/reference device embodying the invention.

As seen in FIGS. 2–4, the shield holder 110 has a plurality of finger-like projections 114 arranged in a cylindrical shape. Some or all of the projections 114 may include a lip 116 which is engageable with the nose portion 104 of the instrument 100 to attach the device to the instrument. If the shield holder 110 is made from a flexible material, such as a molded plastic, the shield holder 110 can be snapped onto the nose 104 of the instrument 100 so that the lips 116 engage the nose 104.

A multilayer combined contamination shield and calibration target 200 can then be affixed to a front annular surface 112 of the shield holder 110. In a preferred embodiment of the invention, the combined contamination shield and calibration target 200 is attached to the shield holder 110 with a layer of adhesive. The combined contamination shield and calibration target 200 may include a user graspable tab 202 for removing the calibration target after a calibration or reference operation has been performed.

Figure 13:
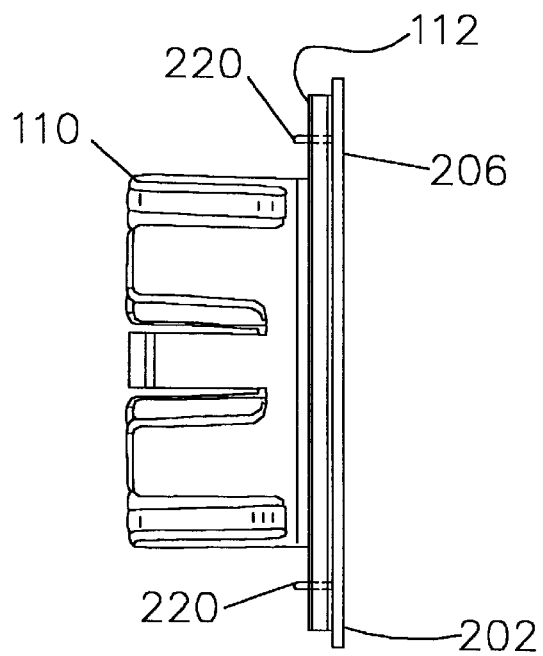
FIG. 13 is a side view of another calibration/reference device embodying the invention.

Of course a calibration target 200 could also be mechanically attached to the shield holder 110 by any type of mechanical attachment mechanism such as staples, clips, pins, etc. FIG. 13 shows an embodiment where a calibration target 206 is attached to a shield holder 110 with a plurality of pins 220 arranged around the periphery of the shield holder 110.

In an alternate embodiment, as shown in FIG. 4, an infection shield 204 may be separately mounted to the shield holder 110. The infection shield 204 could simply be a clear plastic portion of the shield holder 110, which is integrally molded with the shield holder 110. The infection shield 204 could also be a substantially transparent film that is attached to the shield holder 110. A calibration target 206 could then be attached to the front annular surface 112 of the shield holder 110 via an adhesive layer or some type of mechanical attachment device. The calibration target 206 would include a user graspable tab 202 for aiding removal of the calibration target after a calibration or reference operation has been performed.

Figure 5:
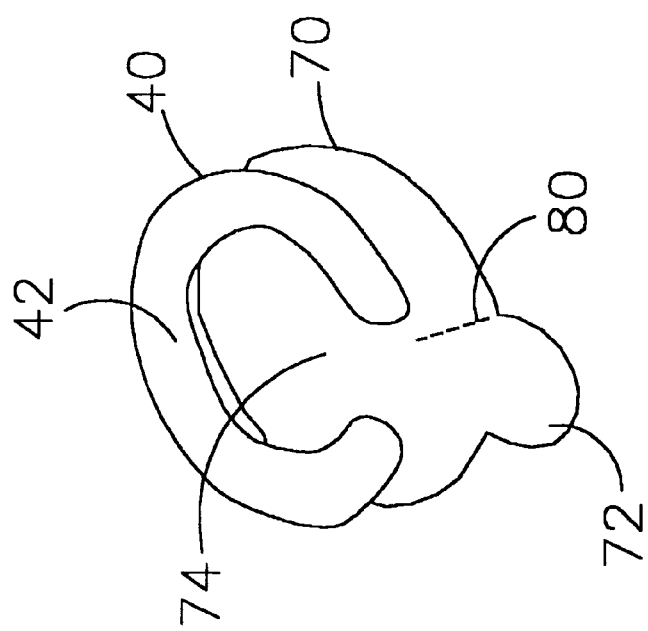
FIG. 5 is an exploded perspective view of a calibration target embodying the invention.

A calibration/reference target embodying the invention is shown in FIG. 5. The target includes a calibration layer 70 having a central portion 74 with known optical properties. A user graspable tab 72 is formed as a part of the calibration layer 70. Also, a double-sided adhesive layer 40 is used to attach the calibration layer 70 to a shield holder 110, as shown in FIG. 4. In alternate embodiments, the adhesive layer 40 can be used to attach the calibration layer 70 to an infection/contamination shield layer which is then attached to the shield holder 110, as shown in FIG. 3. In still other embodiments, the double-sided adhesive layer 40 could be replaced with an adhesive that is applied to the calibration layer 70 or a shield holder 110 in a liquid, gel or paste form.

The calibration layer 70 and the double-sided adhesive layer 40 are carefully constructed so that when the calibration target is removed from a shield holder, the target portion 74 in the center of the calibration layer 70 will tear in a predetermined manner. To that end, the calibration layer 70 may include a reduced strength portion 80, which could be a slit, a perforation or a crease. The reduced strength portion 80 in the embodiment shown in FIG. 5 is a perforation that extends from a peripheral edge of the calibration layer 70, towards the central area 74. When a user grasps the tab 72 and pulls on the tab to remove the calibration layer 70 from a shield holder, the calibration layer 70 will tend to tear along the reduced strength portion 80.

In the embodiment shown in FIG. 5, the adhesive layer 40 has a horseshoe shape such that a portion of the calibration layer 70 having the reduced strength portion 80 is aligned with the gap in the adhesive layer 40. Also, in a preferred embodiment, a first side 42 of the adhesive layer 40 will have a relatively low adhesive strength, and the opposite side of the adhesive layer 40 will have a greater adhesive strength. In this configuration, the lower adhesive strength side 42 of the adhesive layer 40 is used to attach the calibration layer 70 to a shield holder. When a user pulls on the tab 72 to remove the calibration layer 70, the lower adhesive strength side 42 will separate from the shield holder before the higher adhesive strength side separates from the calibration layer 70. Thus, the adhesive layer 40 is fully removed along with the calibration layer 70. Also, because of the gap in the adhesive layer 40, the portion of the calibration layer immediately to the right of the reduced strength portion 80 will tend to remain attached to the shield holder while the portion of the calibration layer 70 adjacent the tab and located beneath the gap in the adhesive layer 40 will pull upward and away from the shield holder. This will cause the calibration layer 70 to begin to tear along the reduced strength portion 80. As the user continues to pull on the tab 72, the tearing of the calibration layer 70 will tend to continue across the center portion 74 having the optical properties used to perform a calibration operation.

If a liquid, gel or paste adhesive is used to attach the calibration layer 70 to a shield holder 110, there will not be varying adhesive strengths. However, in such an embodiment it would be advantageous if the adhesive had a greater affinity for the calibration layer 70 than for the shield holder 110. In this case, most, if not all, of the adhesive would remain attached to the calibration layer 70 as it is removed from the shield holder 110. Thus, no adhesive remaining on the shield holder 110 would contact the skin of a patient or a surface to be measured when the instrument and attached shield holder 110 are used to take a measurement.

Similarly, if some type of mechanical attachment mechanism is used to attach the calibration layer 70 to a shield holder 110, it may be advantageous if the mechanical attachment mechanism is more firmly attached to the calibration layer 70 than to the shield holder 110. This would result in the attachment mechanism being removed from the shield holder along with the calibration layer, leaving the shield holder 110 free of any protrusions when used to take a measurement. For instance, in the embodiment shown in FIG. 13, the pins 220 attaching the calibration target 206 to the shield holder 110 could be more firmly attached to the calibration target than the shield holder 110. The cylindrical shafts of the pins 220 would extend through the annular portion 112 of the shield holder 110. Ends of the pins 220 that protrude out the back side of the annular portion 112 could have a slightly enlarged diameter, thus holding the pins 220 and the attached calibration target 206 firmly to the shield holder 110. When the user pulls the calibration target 206 away from the shield holder 110, the pins 220 will pull out of the holes in the annular portion 112. Also, by arranging the pins in a particular orientation with respect to the user graspable tab 202 of the calibration target 206, the calibration target can be caused to tear or separate in a predetermined manner.

Once a calibration layer 70 has been completely removed from a shield holder, the central portion 74 of the calibration layer 70 should be irrevocably damaged so that the calibration layer 70 cannot be re-used for a new calibration operation. In the embodiment shown in FIG. 4, because the side of the adhesive layer 40 in contact with the calibration layer 70 has a greater adhesive strength than the side 42 which was attached to the shield holder, all of the adhesive layer should remain attached to the calibration target and be removed from the shield holder along with the calibration layer 70.

As mentioned above, the calibration target shown in FIG. 5 is intended to be used with a shield holder 110 as shown in FIG. 4. This type of shield holder 110 includes its own integral infection/contamination shield 204.

Figure 6:
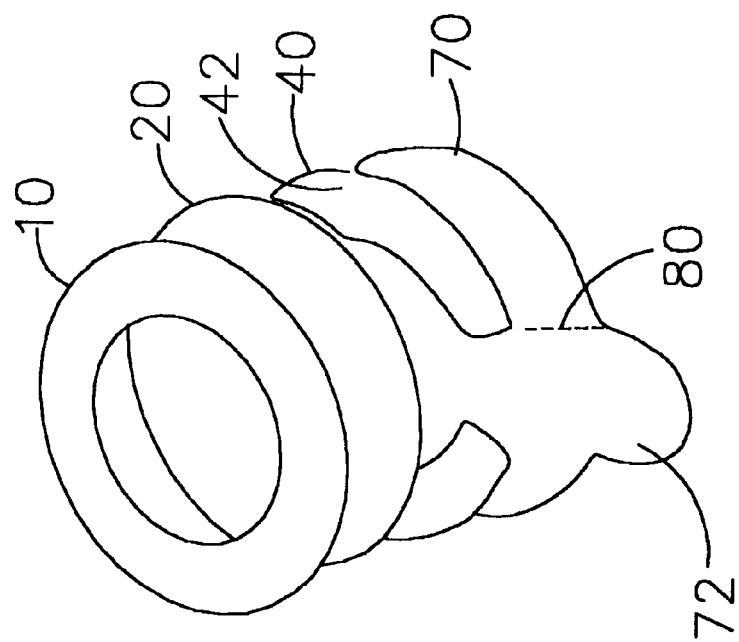
FIG. 6 is an exploded perspective view of a calibration/reference target and an infection shield embodying the invention.

In an alternate embodiment, as shown in FIG. 6, both a calibration target and an infection/contamination shield are attached to the exterior of a shield holder. In this embodiment, a first double-sided adhesive layer 10 is attached to a front edge 112 of a shield holder 110, like the one shown in FIG. 3. The opposite side of the adhesive layer 10 is then attached to an infection/contamination shield 20.

In a preferred embodiment, the infection/contamination shield 20 is substantially transparent. An adhesive layer 40 and a calibration layer 70 are then attached to the infection shield 20. The adhesive layer 40 and the calibration layer 70 have generally the same properties as those described for the embodiment shown in FIG. 5. That is, a first side 42 of the adhesive layer 40 has a relatively low adhesive strength, and the opposite side of the adhesive layer, which is attached to the calibration layer 70, has a greater adhesive strength. Thus, when a user pulls the tab 72 of the calibration layer 70 and removes the calibration layer, both the calibration layer 70 and the adhesive layer 40 are removed. This leaves just the infection/contamination shield 20 attached to the shield holder 110 and the instrument 100. Of course the double-sided adhesive layers 10 and 40 could also be replaced with a liquid, gel or paste adhesive, or with a mechanical attachment device, as described above.

Once a calibration/reference operation has been conducted, and the calibration target is removed, the instrument can be used to conduct a measurement on a patient or an object. Light generated by the instrument passes through the infection shield 20, strikes the patient or object, and is reflected back through the infection shield 20 to a detector of the device. After a patient or object measurement has been completed, the shield holder 110 and the attached infection shield 20 are removed from the instrument 100 and disposed of.

The calibration layer 70 can have a reduced strength portion 80 configured in many different ways. In the embodiments shown in FIGS. 5 and 6, the reduced strength portions extend from a peripheral edge towards a center 74 of the calibration layer 70. This encourages the calibration layer to tear across the center 74 of the calibration layer 70, which is the portion having optical properties used to calibrate a measuring instrument. In preferred embodiments, the reduced strength portion 80 does not extend beyond the annular radial width of the adhesive layer 80 so that light cannot penetrate through the calibration layer 70 and affect a calibration or reference operation.

Figure 8:
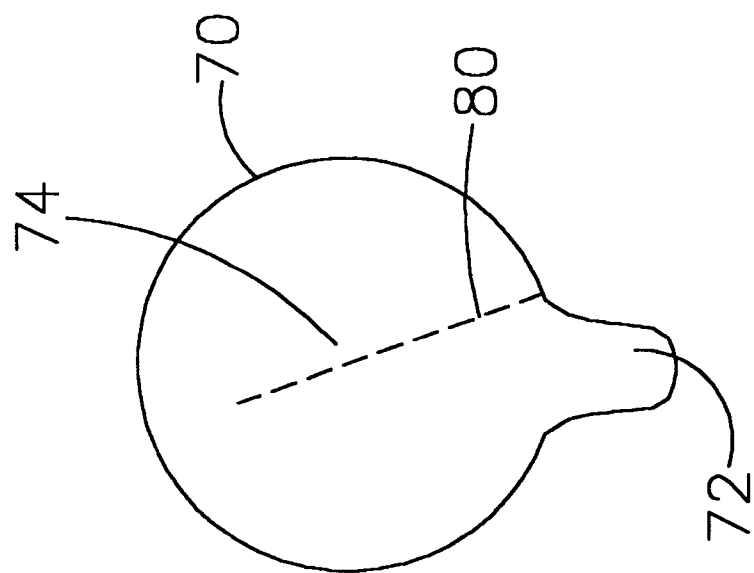
FIG. 8 is a plan view of another calibration/reference target embodying the invention.
Figure 7:
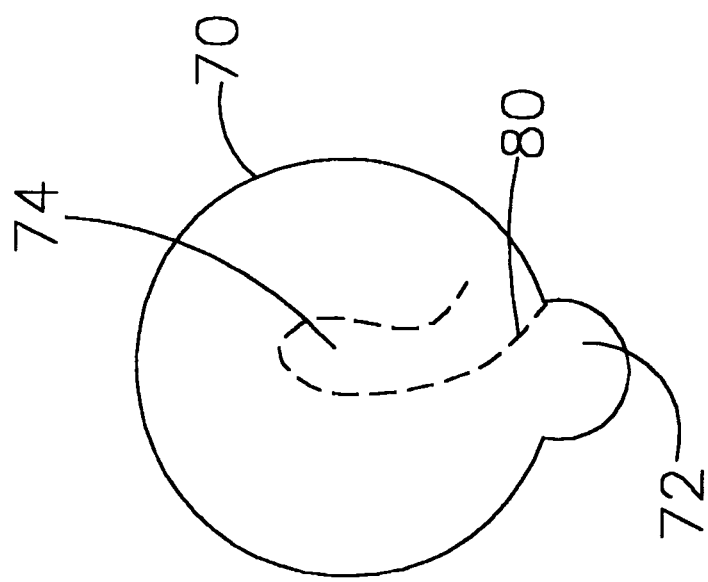
FIG. 7 is a plan view of a calibration/reference target embodying the invention.

In alternate embodiments, as shown in FIGS. 7 and 8, the reduced strength portion can have different configurations. In the embodiment shown in FIG. 7, the reduced strength portion 80 traverses a path across the central region 74 of the calibration layer 70. In the embodiment shown in FIG. 8, the reduced strength portion 80 proceeds in a direct line across the center 74 of the calibration layer 70. Each of these embodiments is intended to ensure that as the calibration layer 70 is removed, the central portion 74 used to calibrate the instrument is altered in a destructive manner so that the calibration layer cannot be reused.

Figure 12:
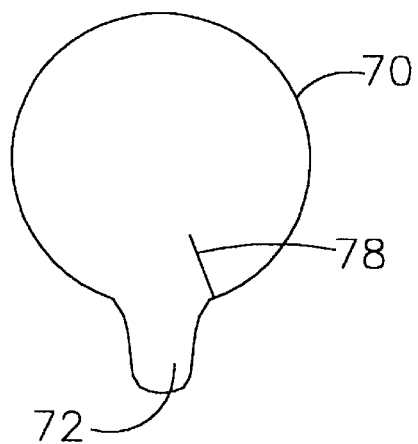
FIG. 12 is a plan view of another calibration/reference target embodying the invention.

In still other embodiments, a cutting device could be incorporated into the calibration layer 70, or into the shield holder 110 or the instrument itself. One such embodiment is shown in FIG. 12, where a wire or monofilament 78 is attached to or embedded in the calibration layer 70. The wire or monofilament 78 will cause the calibration layer 70 to tear in a predetermined manner when a user pulls on the tab 72. Although FIG. 12 shows the wire or monofilament extending only partway across the calibration layer 70, the wire or monofilament could extend further or completely across the calibration target 70. The wire or monofilament could also be arranged in a pattern, like the reduced strength portion 80 shown in FIG. 7.

Figure 14:
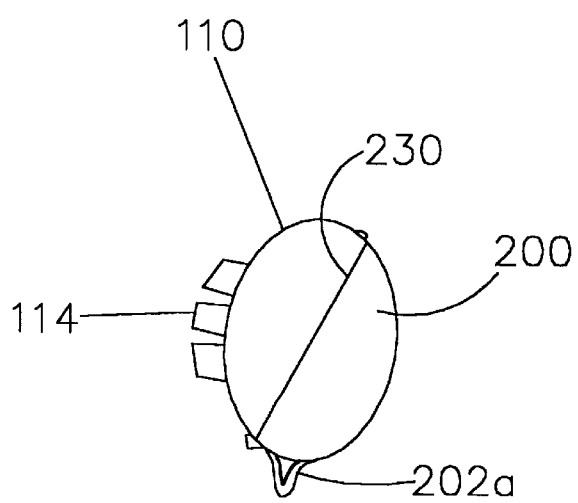
FIG. 14 is a perspective view of another calibration/reference device embodying the invention.

In alternate embodiments, a wire or monofilament could also be attached to the shield holder. In the embodiment shown in FIG. 14, a wire or monofilament 230 is stretched across the back of the calibration layer 200, with ends of the wire or monofilament being attached to the shield holder 110. Also, the wire or monofilament 230 could be replaced with any other type of cutting device that will cause the calibration layer 70 to tear or separate in a predetermined manner when being removed from a measuring instrument.

If the measuring instrument 100 which is used in conjunction with a device embodying the invention is configured so that only a single patient or object measurement may be conducted after each calibration operation, a calibration device embodying the invention can help to prevent patient infection or patient or object cross-contamination.

When a user attempts to use the measuring instrument, a shield holder with an infection/contamination shield and a calibration target will first be attached to the instrument 100. Next, a calibration/reference operation will be performed. Once the calibration/reference operation is complete, the user will grasp a tab 72 on the calibration target and pull on the tab to remove the calibration target. This will cause the calibration target and any attached adhesive layer to be removed from the shield holder. The act of removing the calibration target will destroy at least the portion of the calibration target having the optical properties used to calibrate/reference the instrument 100. Thus, it will be impossible to reuse the calibration target. The user would then proceed to conduct a patient or object measurement with the shield holder and infection shield still attached to the instrument 100. The results of the measurement can then be noted or recorded.

Because the instrument will not perform a second patient or object measurement without first performing another calibration/reference operation, the user will be forced to remove both the shield holder and the infection shield and replace it with a new device that includes a new infection shield and a new calibration target. The user will be forced to perform another calibration operation before the device can be used to perform another patient or object measurement. For this reason, it should be impossible for the device to be used to take two measurements on two different patients or objects using the same shield holder and infection/contamination shield. This prevents cross-contamination between different patients or objects.

Also, an interlock mechanism in the nose of the measuring instrument may interact with a shield holder of a device embodying the invention to inform the instrument when a shield holder is removed. The instrument can then be configured so that no patient measurements can be performed once a shield holder has been removed from the instrument. This should discourage users from attempting to conduct a measurement without an infection/contamination shield in place, thereby reducing the opportunity for patient or object cross-contamination. Similarly, the interlock mechanism could be configured to prevent more than one patient or object measurement cycle from being performed before a shield holder is removed and another one is inserted.

Figure 9:
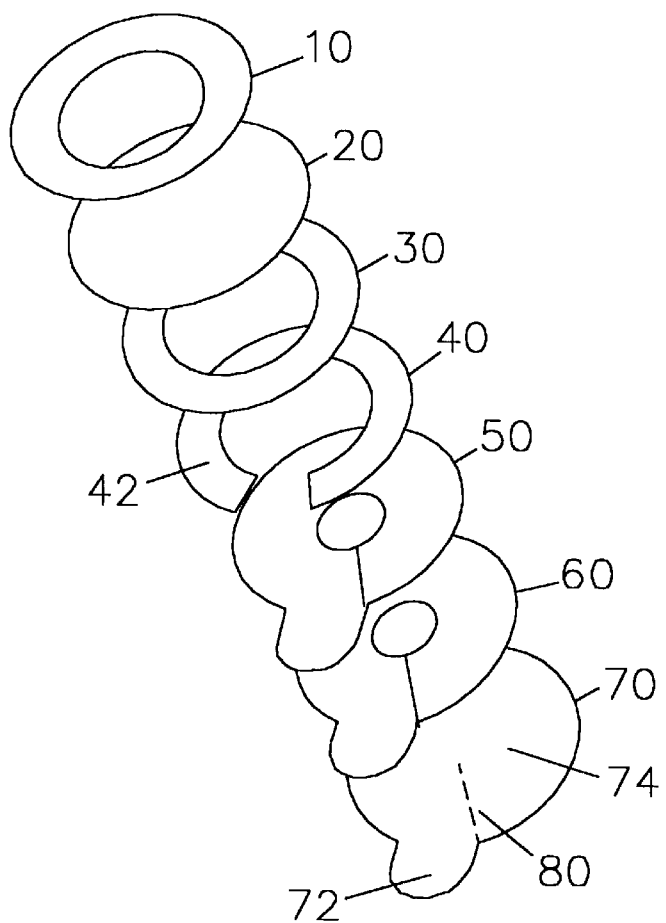
FIG. 9 is an exploded perspective view of a calibration/reference target and infection shield embodying the invention.

In a preferred embodiment of the invention, the shield holder is configured as shown in FIG. 3, and a combined infection/contamination shield and calibration target 200 will be constructed as shown in FIG. 9. In this embodiment, a first double-sided adhesive layer 10 is used to attach the combined infection/contamination shield and calibration target to the shield holder 110. The opposite side of the double-sided adhesive layer 10 is adhered to a shield layer 20. Next, a clear release liner 30 is attached to the infection/contamination shield 20. The release liner 30 will remain permanently attached to the infection shield 20, but will provide a controlled release of the remaining portions of the combined infection shield and calibration target.

Next, a second double-sided adhesive layer 40 is attached to the release liner 30. As in the previous embodiments, a gap is formed in the adhesive layer 40. Next, a spacer layer 50 is attached to the opposite side of the second adhesive layer 40. The spacer layer 50 serves to space a calibration layer a precise distance from an emitting end of an instrument to which the device is attached. A third double-sided adhesive layer 60 then attaches a calibration layer 70 to the spacer layer 50. Of course, the double sided adhesive layers 10, 40 and 60 could all be replaced with a liquid, gel or paste adhesive, or by a mechanical attachment device, as explained above.

The central portion 74 of the calibration layer 70 will be exposed to light emitted by an emission end of an instrument to which the device is attached. Also, reduced strength portions are formed in the spacer layer 50, the third double-sided adhesive layer 60 and the calibration layer 70. As explained above, the reduced strength portions cause the calibration layer 70 to tear in a predetermined manner when the calibration layer 70 is removed from the remaining portions of the device. Also, the reduced strength portions are oriented in a predetermined manner with respect to the gap in the second double-sided adhesive layer 40. Preferably, the reduced strength portions are positioned adjacent one side of the gap. When the device is oriented in this manner, pulling on the tab 72 of the calibration layer 70 causes the calibration layer to tear along the reduced strength portion 80 and to irrevocably damage the central portion 74 of the calibration layer 70.

Of course, the reduced strength portions could also be replaced by a cutting device, as explained above, to cause the calibration layer to tear or separate in a predetermined manner.

Figure 1:
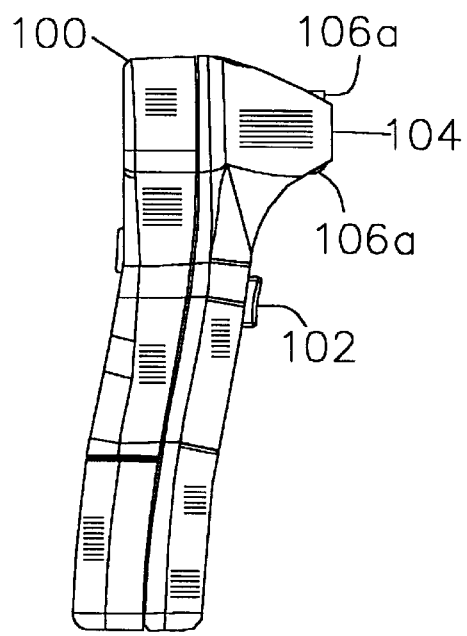
FIG. 1 is a side view of a measuring instrument embodying the invention that can be used with a calibration/reference device embodying the invention.
Figure 10:
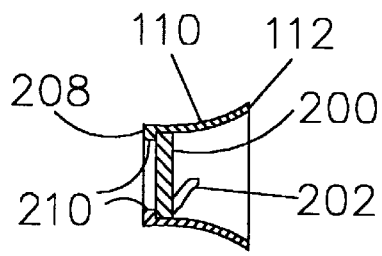
FIG. 10 is a sectional view of another calibration/reference device embodying the invention.

In an alternate embodiment of the invention, the shield holder could be configured as shown in FIG. 10. In this embodiment, the narrower portion of the shield holder is to be attached to a measuring instrument, and the larger diameter flared portion 112 extends away from the device. A flexible annular ring of material 210 on the rear of the shield holder may engage projections 106*a* on the nose portion 104 of a measuring instrument 100, as shown in FIG. 1. In this embodiment, a combined infection/contamination shield and calibration target 200 is located adjacent the back side 208 of the shield holder 110, instead of being located on the front end 112. The combined infection/contamination shield and calibration target 200 still includes a user graspable tab 202 which can be pulled to remove the calibration target. This embodiment, like the embodiment shown in FIG. 4, could have an infection shield mounted on the shield holder and a separate calibration target which is adhered to the shield holder or the infection/contamination shield.

Figure 11A:
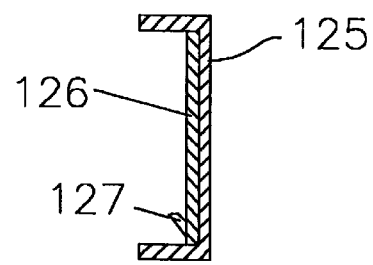
FIG. 11A is a sectional view of a calibration/reference device embodying the invention.
Figure 11B:
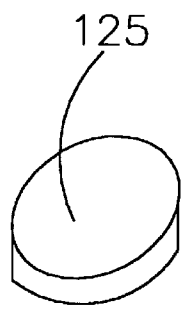
FIG. 11B is a perspective view of an exterior of the calibration/reference device shown in FIG. 11A.

Another alternate embodiment of a calibration/reference device is shown in FIGS. 11A and 11B. In this embodiment, a reference target holder 125 has a cup-like shape. A calibration target 126 may be mounted on the inside of the holder 125, as shown in FIG. 11A. Alternatively, if the holder 125 is transparent, the calibration target 126 could be mounted on the outside of the holder 125. The holder 125 could be formed of any rigid or semi-rigid material. In a preferred embodiment, the holder 125 would be made of molded plastic. The calibration target 126 could be pre-mounted on the holder 125, such that the entire assembly can be used for a period of time, then discarded. Alternatively, the calibration target 126 could be removably mounted on the holder 125, such that the holder 125 can be re-used multiple times with different calibration targets 126. In this instance, the calibration target 126 could include a user graspable tab 127 that aids removal of the calibration target 126 from the holder 125.

To use this type of calibration device, the user would place the calibration device over the detector of a measuring instrument. For instance, the calibration device could be placed over the nose 104 of the measuring instrument 100 shown in FIG. 1. The measuring instrument would then conduct a calibration operation using a portion of the calibration target 126 having known optical properties. The user would then remove the calibration device from the measuring instrument and conduct a measurement on a target object or tissue.

An embodiment like the one shown in FIGS. 11A and 11B could be used with a measuring device that does not require a calibration operation to be performed prior to each measurement. This embodiment could be used for periodic calibration of a measuring device. The holder would ensure that the calibration target is correctly positioned relative to the light source and detector of the measuring instrument. Also, the sidewalls of the holder 125 would serve to block outside light from reaching a detector of the device, thereby ensuring the calibration operation is accurate.

In a preferred embodiment of the device, the calibration target 126 would be removably mounted on the holder 125. The user would obtain a calibration target 126 and first place the calibration target 126 on the inside of the holder 125. The user would then conduct a calibration operation as described above. After the calibration operation has been performed, the user could remove the calibration target 126 from the holder 125 using the user graspable tab 127, so that the holder can be reused with another calibration target 126.

Either of the calibration targets shown in FIGS. 5 and 6 could be used with the holder 125 shown in FIGS. 11A and 11B. If the calibration target shown in FIG. 5 is used, and the calibration target is attached to the inner side of the holder 125 (as shown in FIG. 11A) the double sided adhesive layer 40 could be used to attach the calibration layer 70 to the inside of the holder 125. In this instance, the calibration layer 70 would have known optical properties on the side of the calibration layer 70 opposite the adhesive layer 40, which is the side that would face the detector of a measuring instrument. If the calibration target is attached to the outside of the holder 125 (not shown), the calibration layer 70 of the calibration target would have known optical properties on the side facing the adhesive layer 40, and the holder 125 would be at least partially transparent.

If the calibration target shown in FIG. 6 is used, an additional adhesive layer on the side of the calibration layer 70 opposite the adhesive layer 40 could be used to attach the calibration device to the inside of the holder 125. In this instance, when the holder is placed over the output end of the measuring instrument, the double sided adhesive layer 10 would be pressed against and adhere to the measuring instrument. Then, after a calibration operation has been performed, when the holder 125 is removed from the measuring instrument, it will leave the entire calibration target attached to the measuring instrument. The user would then remove the calibration layer 70, and its attached adhesive layer 40, so that the shield layer 20 and the double sided adhesive layer 10 remain attached to the measuring instrument. The instrument could then be used to conduct measurements, and the shield layer 20 would act as a contamination or infection shield Also, in alternative embodiments, the adhesive strength of the adhesive layers could be designed such that removal of the cover 125 from the measuring instrument, after a calibration operation, will cause the calibration layer 70 and adhesive layer 40 to also be removed from the measuring instrument. This would leave the measuring instrument, with the shield layer 20 and adhesive layer 10, ready to perform a measurement operation. The user could then remove the calibration layer 70 from the holder 125 so that the holder 125 can be re-used. Alternatively, the holder 125 and the attached calibration layer 70 and adhesive layer 40 could simply be discarded.

Figure 15:
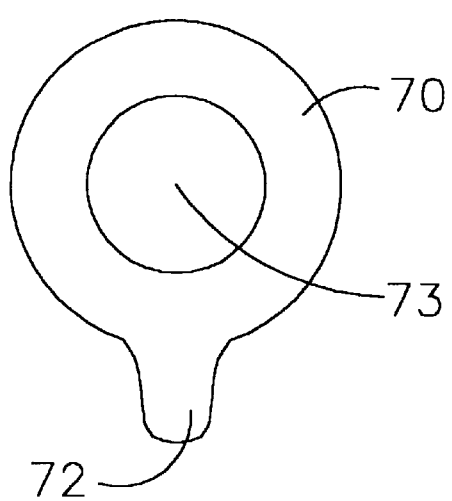
FIG. 15 is a plan view of another calibration/reference target embodying the invention.

Also, in some embodiments of the calibration devices described above, the portion of a calibration/reference target having known optical properties need not be simply reflective/scattering. In an alternate embodiment, a target layer of a calibration device embodying the invention could include a fluorescent portion which emits fluorescent electromagnetic radiation in response to an excitation light. An embodiment of a fluorescent calibration layer is shown in FIG. 15. In this embodiment, a fluorescent portion 73 is centered on the calibration layer 70.

When a calibration device that includes a fluorescent calibration layer is attached to a measuring instrument, light from a light source of the measuring instrument can be used to excite the fluorescent portion 73. The fluorescent portion 73 would then emit fluorescent light, which can be detected by a detector of the measuring instrument. The fluorescent light emitted by the fluorescent portion 73 may be at a different wavelength than the light used to excite the emissions. Thus, a fluorescent calibration device can be used to calibrate an instrument for light emissions in a different portion of the spectrum than would be possible with simply a reflective calibration device.

Also, even when a calibration target having a fluorescent portion is used, by selectively receiving only the same wavelengths that were emitted by the measuring instrument, one can conduct a calibration based on scattered light. By selectively receiving only the wavelengths corresponding to fluorescent light generated by a target, one can conduct a calibration operation based only on the fluorescent light, thereby preventing reflectance/scattering properties of the target from affecting the calibration operation.

Also, a calibration/reference operation performed with a fluorescent calibration/reference target could be designed to determine time characteristics of the fluorescent target. For instance, the fluorescent target could be illuminated with a relatively short duration burst of excitation light, then the fluorescent emissions from the fluorescent target could be monitored to determine how long it takes for an amplitude of the fluorescent emissions to decay below a threshold value. The details of such a method are provided in U.S. Pat. No. 5,348,018 to Alfano et al, the contents of which are hereby incorporated by reference.

In an alternate method of conducting a calibration/reference operation with a fluorescent target, the fluorescent target could be illuminated with an amplitude modulated beam of excitation light. Because an amplitude of the excitation light modulates with time, an amplitude of the fluorescent light would also modulate with time, but at the same frequency. A detector of a measuring instrument could monitor the fluorescent light generated by the fluorescent target and compare the amplitude modulations of the fluorescent light with the amplitude modulations of the excitation light. A phase shift between the excitation light modulation and the fluorescent light modulation provides an indication of the time characteristics of the fluorescent target. Also, a demodulation factor which represents a ratio of the amplitudes of the excitation light to the amplitudes of the fluorescent light could be used, in conjunction with the phase shift, to determine properties of the fluorescent calibration device. Details of such a method are provided in U.S. Pat. No. 5,628,310 to Rao et al., the contents of which are hereby incorporated by reference.

In still other methods of using a fluorescent calibration/reference target, rotation of polarization of fluorescent light generated by the target, with respect to a polarization plane of the excitation light, can be used to determine time characteristics of the fluorescent target. In this method, a polarized excitation light would illuminate the fluorescent target. The detector mechanism of the measuring instrument would be configured to determine a polarization orientation of fluorescent light output by the fluorescent target in response to the excitation light. The amount of polarization rotation of the fluorescent light, with respect to the polarization plane of the excitation light could also be used to determine time characteristics of the fluorescent target. Details of such a method are provided in U.S. Pat. No. 5,515,864 to Zuckerman, the contents of which are hereby incorporated by reference.

Figure 16:
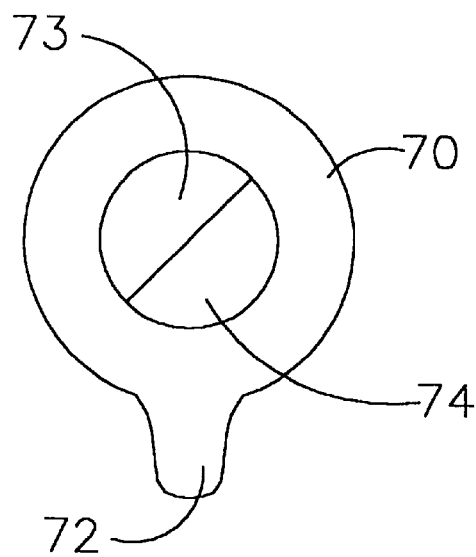
FIG. 16 is a plan view of another calibration/reference target embodying the invention.

In yet another embodiment of the invention, as shown in FIG. 16, a calibration layer 70 includes a central region having a fluorescent portion 73 and a portion 74 having known scattering/reflection properties. When a calibration device including a calibration layer as shown in FIG. 16 is mounted on a measuring instrument, light emitted from a light source of the instrument can both scatter/reflect off the portion 74 having known properties, and the light can excite fluorescent emissions from the fluorescent portion 73. The scattered or reflected light, and fluorescent emissions from the fluorescent portion 73 can be detected by a detector of the measuring instrument and used to calibrate or reference the instrument.

Figure 17:
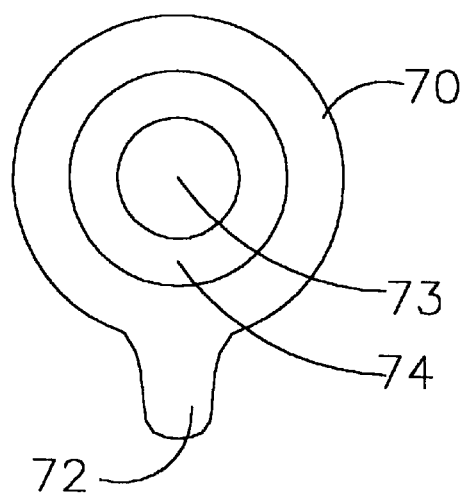
FIG. 17 is yet another embodiment of a calibration/reference target embodying the invention.

In still another embodiment, as shown in FIG. 17, a fluorescent portion 73 may be centered within a region 74 having known scattering/reflective properties. Alternatively, the portion having known scattering/reflective properties could be centered in a larger fluorescent portion. When a target layer 70, as shown in FIG. 17, is incorporated in a calibration device embodying the invention, both light scattered by the portion 74 and fluorescent light emitted by the fluorescent region 73 can be used in a calibration or reference operation.

The two portion calibration layers 70 shown in FIGS. 16 and 17 allow for a calibration operation to rely on light having different wavelengths. The light reflected from the portion 74 having known optical properties will be at the same wavelength as the light emitted by the measuring instrument. Fluorescent light generated by the fluorescent portion 73 will be at a different wavelength. This type of calibration/reference operation could be particularly useful for measuring instruments that utilize light at more than one wavelength to conduct a measurement operation. This type of calibration/reference operation could also be useful for a device that utilizes both fluorescent light generated by a target object, and light that is scattered or reflected from the target object to conduct a measurement operation.

In still other embodiments of the invention, the target layer 70 may be partially transmissive so that light transmitted through the target layer can be used to perform a calibration or reference operation. For instance, in the embodiment shown in FIG. 5, the central region could have known transmissive properties so that light transmitted through the central region 74 may be used to perform a calibration or reference operation. The amplitude of the transmitted light at one or more wavelengths could be detected, or the polarization characteristics of the transmitted light could be detected, as described above. Two methods for performing a calibration or reference operation using a transmissive calibration target will now be described with reference to FIGS. 18, 19, 20A and 20B.

Figure 18:
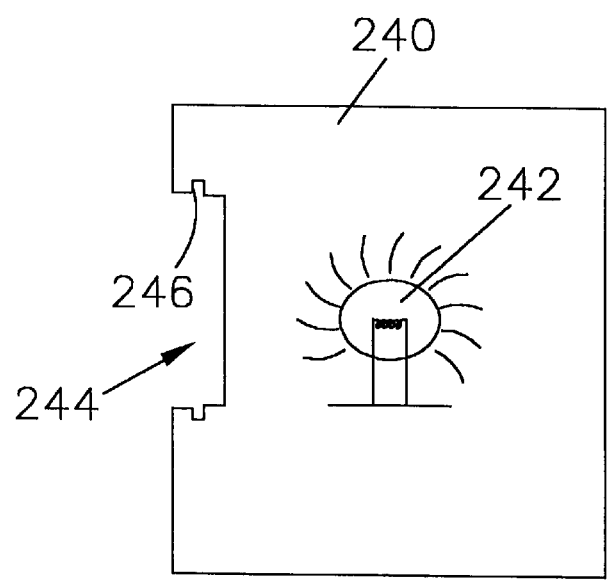
FIG. 18 is a diagram of an external light source that can be used with a measuring instrument and transmissive calibration/reference device embodying the invention.

FIG. 18 shows an external light source that can be used to perform a transmissive calibration or reference operation, and to conduct a transmissive measuring operation. The external light source 240 includes a light source 242, which can be in the form of an incandescent or fluorescent bulb, a light emitting diode, a laser, or any other device capable of generating electromagnetic radiation. An aperture 244 allows light from the light source 242 to escape the device. A slot 246, or any other type of mechanical attachment mechanism, can be used to mount a sample to be measured in the aperture 244 of the light source 240.

Figure 19:
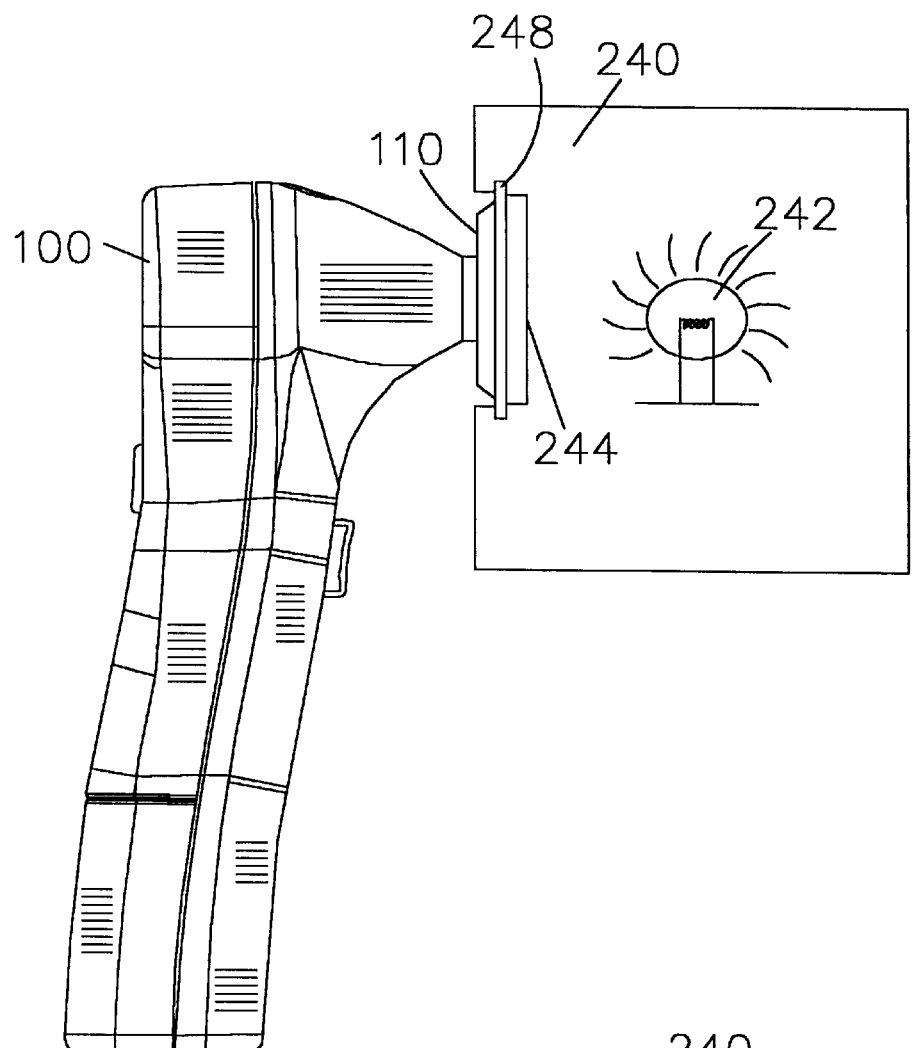
FIG. 19 is a diagram showing a measuring instrument embodying the invention performing a calibration operation or a measurement operation utilizing an external light source.

FIG. 19 shows a measuring instrument 100 being used to conduct a calibration or measurement operation using the external light source 240. If a calibration operation is to be performed, the light source 242 is turned on, and a calibration or reference device is mounted on the measuring instrument 100. The calibration device would include a calibration/reference target mounted on a shield holder 110. The calibration device is then pressed against the aperture 244 of the external light source 240. Light from the light source 242 passes through the aperture, and a portion of the light also passes through the calibration device. The light transmitted through the calibration device is received by a detector within the measuring instrument 100 and used to conduct a calibration or reference operation. In some embodiments of the device, a clear window 248 may be mounted in the aperture 244, and the calibration target may be pressed directly against the window 248.

Once a calibration or reference operation has been successfully performed, the calibration layer of the calibration device would be removed so that the device is ready to conduct a patient or object measurement. Removal of the calibration device could leave a shield holder 110 and an associated infection shield attached to the measuring instrument 100. An object to be measured may then be mounted on a slide 248 that is inserted into the aperture 244 of the external light source 240. The shield holder 110, without the calibration target, would then be pressed against the slide 248, and the measurement device would be activated to conduct a measurement. Light from the light source 242 would pass through the slide 248, the sample mounted thereon, and the infection shield and shield holder 110, and the transmitted light would be detected by a detector of the measuring instrument 100. The transmitted light would then be used to conduct a measurement operation.

This type of an embodiment could be useful for measuring optical properties or colors of objects capable of being mounted on slides 248 that are inserted into an external light source 240. In alternate embodiments, the measurement operation could be performed directly on an object without the use of the external light source 240. In this embodiment, the external light source 240 would be used only to perform a calibration or reference operation with a transmissive calibration target.

In the embodiment shown in FIGS. 20A and 20B, a light source of the measuring instrument would be used to conduct a transmissive calibration and/or measuring operation. The measuring instrument 100 would include a means for applying light to a calibration/reference target mounted on the instrument 100. The means could include a light source inside the instrument 100 which transmits light through an optical fiber to a light head 250. In alternate embodiments, the light head 250 could include an integral light source. In either event, the light head 250 may be attached to a retractable tether 252 for holding the light head 250 in place on top of the instrument 100 when it is not in use. If an optical fiber is used to conduct light from a source inside the instrument to the light head 250, the optical fiber could be inside the tether 252.

With an embodiment like the one shown in FIGS. 20A and 20B, a shield holder 110 and an attached transmissive calibration target would be mounted on a nose portion 104 of the measuring instrument 100. Next, the retractable light head 250 would be pulled out of the device and placed over the transmissive calibration target attached to the shield holder 110. The device would then be activated so that light is emitted from the light head 250, is transmitted through the transmissive target, and is detected by a detector of the instrument 100 so that a calibration/reference operation may be performed.

Once a calibration/reference operation has been performed, the light head 250 could then be retracted back into the measuring instrument, and the calibration target would be removed from the shield holder 110. This would place the instrument in a condition ready for a patient or object measurement. The measurement operation could be conducted such that light emitted from the nose portion 104 of the instrument is reflected/scattered from the target object and is detected by the instrument. Alternatively, the light head 250 could be used to provide light for a measurement operation.

In some of the embodiments described above, a calibration operation has relied on light that is reflected or scattered from, or transmitted through, a portion of a calibration target having known optical properties. This could involve determining an amplitude of the reflected/scattered/transmitted light at one or more wavelengths. In other devices and methods embodying the invention, the radiation output to the calibration target could have a particular polarization orientation. The measuring instrument could then be configured to determine a polarization orientation of the reflected/scattered/transmitted light. Such a method could rely on the relative attenuation of a polarized or depolarized component of reflected/scattered/transmitted light, or an extent of depolarization.

In yet another embodiment of the invention, a plurality of emitter and detector pairs could be arranged in an array on a measuring instrument. During a calibration operation using any of the calibration devices described above, the light output from the emitters could reflect/scatter/transmit through portions of the calibration device and impinge on the respective detectors. If a fluorescent calibration target is used, fluorescent light from the target could impinge on the detectors. After the calibration operation is conducted, the same emitter/detector pairs could be used to interrogate multiple points on a target material or tissue. Such a configuration would allow the measuring instrument to develop an image of the target material or tissue, or an image of reflective/transmissive/fluorescent properties of the target.

In still other embodiments, one or more light sources could illuminate/excite a target material or tissue, and reflected/scattered/transmitted light, or fluorescent light, passing from the target material or tissue could impinge on a detector array configured generate an image of the material or tissue, or an image of the reflective/transmissive/fluorescent properties of the target material or tissue. For instance, a charged coupled device (CCD) could be used as the detector array. The calibration devices described above could be used to calibrate or reference a measuring instrument that utilizes such a detector array.

Many variations could be made to the embodiments described above without departing from the spirit or scope of the present invention. For instance, although each of the embodiments shown in FIGS. 2–20A and 20B have a shield holder and a calibration/reference target that is generally circular or annular in shape, any other shape could be used without departing from the invention. For instance, the shield holder, infection shield and calibration target could be rectangular, square, or any other shape necessary to conform to the shape of the instrument to which the device is attached.

Also, the calibration layers 70 of the embodiments described above could have any type of optical, transmissive or fluorescent properties used to conduct a calibration or reference operation. As mentioned above, use of the term "calibration target" in the specification and claims is intended to encompass both calibration targets and reference targets. Likewise, use of the term "calibration operation" is intended to encompass both calibration and reference operations.

In any one embodiment of the invention, the calibration layer would have very specific reflective, transmissive and/or fluorescent properties. However, calibration/reference targets embodying the invention might include different types of calibration layers having different reflective/transmissive/fluorescent properties. For instance, colored calibration targets could be provided in a variety of different skin tones. A calibration device embodying the invention could then be selected by a user based on a patient's skin tone or age, and the selected calibration target could be used to calibrate an instrument.

Also, the reflective/transmissive/fluorescent properties of the target may be selected such that the instrument can be calibrated/referenced at the mean or the median of the expected measurement range. Such a strategy will provide maximum measurement accuracy since any error is at a minimum for measurements closest to the calibration value. Using the example of the patient skin tone described above, the reflectance of the calibration target can be formulated such that its reflectance matches the median reflectance of the patients expected to be measured with the instrument. As an additional example, the fluorescence lifetime and/or quantum yield of a fluorescent target may be selected such that it equals the median lifetime and/or quantum yield of the fluorescing analyte being measured.

Also, although each of the embodiments described above have a user graspable tab attached to the calibration layer, other types of user graspable tab configurations are possible. For instance, instead of being a tab, a cord, a string or a ring of material could be attached to the calibration layer. For instance, in the embodiment shown in FIG. 14, the user graspable tab 202a is a loop of material whose ends are attached to the calibration layer 200. Each of these items is easy for the finger of a user to grasp and to pull. The invention is intended to include any type of user graspable tab, cord, string, ring, or other device that can be used to remove the calibration layer from the remaining portions of the device.

Furthermore, in the embodiments described above, an infection shield and a calibration target are attached to a shield holder, which in turn is attached to the instrument. Some embodiments of the device may not utilize a shield holder. In these embodiments, the infection shield and/or the calibration target may be directly attached to a measuring instrument. These embodiments may use an adhesive layer or a mechanical attachment device to attach the infection shield and the calibration target to the instrument.

Still further, if the instrument which the device is used with is not used for medical purposes, and infection or cross-contamination is not an issue, a device embodying the invention may simply comprise a calibration layer. The calibration target in FIG. 5 provides an example of such an embodiment. This calibration target could be directly attached to the measuring instrument.

The foregoing embodiments are merely exemplary and are not to be construed as limiting the present invention. The present teaching can be readily applied to other types of apparatus. Many alternatives, modifications, and variations will be apparent to those skilled in the art. In the claims, means-plus-function clauses are intended to cover the structures described herein as performing the recited function and not only structural equivalents but also equivalent structures. For example, although a pin and an adhesive layer may not be structural equivalents, in that a pin employs a cylindrical penetrating structure to secure two parts together, whereas an adhesive layer does not penetrate the parts and extends over a greater surface area, in the environment of fastening two parts together, a pin and an adhesive layer may be equivalent structures.

What is claimed is:

1. A method of calibrating a measuring instrument, comprising the steps of:
   arranging a fluorescent calibration device on a measuring instrument, wherein the fluorescent calibration device includes a structure that is attachable to the measuring instrument and a fluorescent calibration target that is removably attached to the structure;
   conducting a calibration measurement using the fluorescent calibration device; and
   removing at least a portion of the fluorescent calibration device from the measuring instrument.

2. The method of claim 1, wherein the removing step comprises removing the fluorescent calibration target from the structure, and leaving the structure of the fluorescent calibration device attached to the measuring instrument such that radiation can pass through the structure during a subsequent measuring operation.

3. The method of claim 1, wherein the step of conducting a calibration measurement comprises the steps of:
   illuminating the fluorescent calibration target of the calibration device with electromagnetic radiation; and
   measuring electromagnetic radiation passing from the fluorescent calibration target to the measuring instrument.

4. The method of claim 3, wherein the illuminating step comprises illuminating the fluorescent calibration target with electromagnetic radiation having a first wavelength range, wherein the measuring step comprises measuring electromagnetic radiation having a second wavelength range, and wherein the first and second wavelength ranges are not co-extensive.

5. The method of claim 3, wherein the measuring step comprises measuring fluorescent electromagnetic radiation generated by the fluorescent calibration target.

6. The method of claim 5, wherein the measuring step further comprises measuring radiation that is scattered or reflected from the fluorescent calibration target.

7. The method of claim 5, wherein the measuring step comprises measuring a time characteristic of the fluorescent electromagnetic radiation.

8. The method of claim 5, wherein the measuring step comprises measuring a polarization characteristic of the fluorescent electromagnetic radiation.

9. The method of claim 3, wherein the measuring step comprises the steps of:

measuring electromagnetic radiation scattered from the fluorescent calibration device; and measuring fluorescent electromagnetic radiation generated by the fluorescent calibration target.

10. The method of claim 3, wherein the illuminating step comprises illuminating the fluorescent calibration target with a burst of electromagnetic radiation, and wherein the measuring step comprises measuring an amount of time required for fluorescent electromagnetic radiation produced by the fluorescent calibration target in response to the burst of illuminating electromagnetic radiation to decay below a threshold value.

11. The method of claim 1, wherein the step of conducting a calibration measurement comprises the steps of:

illuminating the fluorescent calibration device with amplitude modulated electromagnetic radiation;

measuring electromagnetic radiation passing from the fluorescent calibration device to the measuring instrument; and determining a phase shift between the illuminating amplitude modulated electromagnetic radiation and the electromagnetic radiation passing from the fluorescent calibration device to the measuring instrument.

12. The method of claim 11, wherein the measuring step comprises measuring fluorescent electromagnetic radiation generated by a fluorescent calibration target of the fluorescent calibration device.

13. The method of claim 11, further comprises a step of determining a demodulation factor, wherein the demodulation factor represents a ratio of amplitudes of the illuminating electromagnetic radiation and the electromagnetic radiation passing from the fluorescent calibration device to the measuring instrument.

14. The method of claim 1, wherein the step of conducting a calibration measurement comprises the steps of:

illuminating the fluorescent calibration device with polarized electromagnetic radiation;

measuring electromagnetic radiation passing from the fluorescent calibration device to the measuring instrument; and determining a polarization difference between the illuminating electromagnetic radiation and the electromagnetic radiation passing from the fluorescent calibration device to the measuring instrument.

15. A method of calibrating a measuring instrument, comprising the steps of:

placing a transmissive calibration device over an output end of a measuring instrument;

conducting a calibration operation using the transmissive calibration device wherein the measuring instrument measures transmissive properties of the transmissive calibration device during the calibration operation; and removing at least a portion of the transmissive calibration device from the measuring instrument.

16. The method of claim 15, wherein the removing step comprises leaving a structure of the transmissive calibration device attached to the measuring instrument such that radiation can pass through the structure during a subsequent measuring operation.

17. The method of claim 15, wherein the step of conducting a calibration operation comprises the steps of:

illuminating a portion of the transmissive calibration device with electromagnetic radiation; and measuring electromagnetic radiation passing through the transmissive calibration device.

18. The method of claim 17, wherein the illuminating step comprises illuminating a portion of the transmissive calibration device with electromagnetic radiation generated by the measuring instrument.

19. The method of claim 17, wherein the illuminating step comprises illuminating a portion of the transmissive calibration device with electromagnetic radiation generated by a source external to the measuring instrument.

20. A method of calibrating a measuring instrument having a detector, comprising the steps of:

arranging a fluorescent calibration device on the measuring instrument;

conducting a calibration operation, wherein polarized fluorescent radiation passes from the fluorescent calibration device to the detector of the measuring instrument; and removing at least a portion of the calibration device from the measuring instrument.

21. The method of claim 20, wherein the removing step comprises leaving a structure of the calibration device attached to the measuring instrument such that radiation can pass through the structure during a subsequent measuring operation.

22. The method of claim 20, wherein the step of conducting a calibration operation comprises measuring a polarization characteristic of the polarized fluorescent radiation passing from the fluorescent calibration device to the detector.

23. The method of claim 20, wherein the step of conducting a calibration operation comprises illuminating the fluorescent calibration device with polarized excitation radiation.

24. The method of claim 23, wherein the step of conducting a calibration operation comprises determining a polarization difference between the polarized excitation radiation and the polarized fluorescent radiation passing from the fluorescent calibration device to the detector.

25. A method of conducting a calibrated measurement on a target object with a measuring instrument having an imaging detector array, comprising the steps of:

arranging a calibration device on the measuring instrument;

conducting a calibration operation, wherein radiation passes from the calibration device to the detector array of the measuring instrument;

removing a portion of the calibration device from the measuring instrument while leaving a structure of the calibration device attached to the measuring instrument; and conducting a measurement operation by obtaining an image of the target object based on radiation that passes from the target object, through the structure and to the detector array.

26. The method of claim 25, wherein the measurement operation comprises obtaining an image of at least one of scattering characteristics, fluorescent characteristics and transmissive characteristics of the target object.

27. A calibration device, comprising:
- a structure having an opening through which radiation can pass; and
- a removable calibration target arranged on said opening, wherein the removable calibration target includes a fluorescent portion.

28. The calibration device of claim 27, wherein the structure comprises an adhesive portion configured to adhere the removable calibration target to a measuring instrument.

29. The calibration device of claim 27, wherein the removable calibration target includes at least one reduced strength portion configured such that the removable calibration target will tear or separate along the at least one reduced strength portion when the removable calibration target is removed from other portions of the calibration device.

30. The calibration device of claim 29, wherein the at least one reduced strength portion comprises at least one of a perforation, a crease and a slit.

31. The calibration device of claim 27, further comprising a cutter for causing the calibration target to tear or separate in a predetermined manner when the calibration target is removed from other portions of the calibration device.

32. The calibration device of claim 27, wherein the calibration target includes a user graspable tab that aids a user in removing the calibration target from the structure.

33. The calibration target of claim 27, further comprising a shield layer attached to the structure.

34. The calibration target of claim 33, wherein the shield layer is arranged on the structure such that when the calibration target is removed from the structure, the shield layer remains attached to the structure.

35. A calibration device, comprising:
- a structure having an opening through which radiation can pass; and
- a removable calibration target arranged on said opening, wherein the removable calibration target includes a transmissive portion configured to allow a measurement instrument conduct a calibration operation based on radiation transmitted through the transmissive portion.

36. The calibration device of claim 35, wherein the structure comprises an adhesive portion configured to adhere the removable calibration target to a measuring instrument.

37. The calibration device of claim 35, wherein the removable calibration target includes at least one reduced strength portion configured such that the removable calibration target will tear or separate along the at least one reduced strength portion when the removable calibration target is removed from other portions of the calibration device.

38. The calibration device of claim 37, wherein the at least one reduced strength portion comprises at least one of a perforation, a crease and a slit.

39. The calibration device of claim 35, further comprising a cutter for causing the calibration target to tear or separate in a predetermined manner when the calibration target is removed from other portions of the calibration device.

40. The calibration device of claim 35, wherein the calibration target includes a user graspable tab that aids a user in removing the calibration target from the structure.

41. The calibration target of claim 35, further comprising a shield layer attached to the structure.

42. The calibration target of claim 41, wherein the shield layer is arranged on the structure such that when the calibration target is removed from the structure, the shield layer remains attached to the structure.

43. A calibration device, comprising:
- a calibration target holder configured to be arranged on a measuring instrument and to block external light from reaching a detector of a measuring instrument when the holder is arranged on the measuring instrument; and
- a calibration target having known optical properties that is mountable on the holder.

44. The calibration device of claim 43, wherein the calibration target is removably mountable on the calibration holder.

45. The calibration device of claim 43, wherein the calibration target includes:
- a shield layer; and
- a target layer having known optical properties.

46. The calibration device of claim 45, wherein the calibration device is configured such that when the calibration device is arranged on a measuring instrument, and the target layer is removed, the shield layer remains attached to the measuring instrument.

47. A measuring system for measuring characteristics of a target object, comprising:
- a housing;
- a calibration device that includes a structure and a removable calibration target arranged on the structure, wherein the calibration device is removably attachable to the housing, and wherein the calibration device is configured such that the calibration target can be removed from the structure while the structure remains attached to the housing; and
- a detector array mounted on the housing and configured to detect an image of a target object.

48. The measuring system of claim 47, wherein the system is configured such that during a measurement operation, radiation passes from a target object, through the structure of the calibration device, and to the detector array.

49. The measuring system of claim 47, wherein the system is configured to obtain an image of at least one of scattering characteristics, transmissive characteristics and fluorescent characteristics of a target object.

50. The measuring system of claim 47, wherein the system is configured to conduct a calibration operation using radiation passing from the calibration target to the detector array.

51. A method of calibrating a measuring instrument, comprising the steps of:
- arranging a calibration device on a measuring instrument;
- illuminating the calibration device with polarized radiation;
- detecting a polarization characteristic of light that is scattered or reflected from the calibration device.

52. The method of claim 51, wherein the arranging step comprises arranging a calibration device including a structure and a calibration target on the measuring instrument, and wherein the method further comprises the step of removing the calibration target from the structure while the structure remains attached to the measuring instrument such that radiation can pass through the structure during a subsequent measurement operation.

53. A method of calibrating a measuring instrument, comprising the steps of:
- arranging a calibration device on a measuring instrument, the calibration device including a structure and a calibration target that is removably attached to the structure;
- illuminating the calibration device with polarized radiation;
- detecting a polarization characteristic of light that is scattered from or transmitted through the calibration device; and removing the calibration target from the structure of the calibration device while the structure remains attached to the measuring instrument such that radiation can pass through the structure during a subsequent measurement operation.

54. A method of calibrating a measuring instrument, comprising the steps of:

arranging a fluorescent calibration target on a measuring instrument;

illuminating the fluorescent calibration target with a burst of electromagnetic radiation; and detecting an amount of time required for fluorescent electromagnetic radiation produced by the fluorescent calibration target in response to the burst of electromagnetic radiation to decay below a threshold value.

55. A method of calibrating a measuring instrument, comprising the steps of:

arranging a fluorescent calibration target on a measuring instrument;

illuminating the fluorescent calibration target with amplitude modulated electromagnetic radiation;

measuring electromagnetic radiation passing from the fluorescent calibration target to the measuring instrument; and determining a phase shift between the illuminating amplitude modulated electromagnetic radiation and the electromagnetic radiation passing from the fluorescent calibration target to the measuring instrument.

56. The method of claim 55, further comprising a step of determining a demodulation factor, wherein the demodulation factor represents a ratio of amplitudes of the illuminating electromagnetic radiation and the electromagnetic radiation passing from the fluorescent calibration target to the measuring instrument.

57. A method of calibrating a measuring instrument, comprising the steps of:

placing a removable calibration target in a light blocking device;

placing the light blocking device, with the removable calibration target, over an output end of a measuring instrument;

conducting a calibration operation wherein electromagnetic radiation output from the measuring instrument is scattered from the removable calibration target back to a detector of the measuring instrument;

removing the light blocking device from the measuring instrument; and removing the removable calibration target from the light blocking device.

58. The method of claim 57, further comprising the steps of:

placing the light blocking device, without the removable calibration target, over the output end of the measuring instrument; and conducting a calibration operation wherein electromagnetic radiation output from the measuring instrument is scattered from the light blocking device back to a detector of the measuring instrument.

59. The method of claim 58, further comprising the steps of:

placing a shield layer into the light blocking device after all calibration steps have been performed;

placing the light blocking device over the output end of the measuring instrument; and removing the light blocking device from the measuring instrument while leaving the shield layer attached to the output end of the measuring instrument.

60. The method of claim 59, further comprising a step of removing a release layer from the shield layer after the shield layer has been placed into the light blocking device to expose an adhesive on the shield layer, and wherein the step of placing the light blocking device over the output end of the measuring instrument causes the shield layer to adhere to the output end of the measuring instrument.

61. The method of claim 57, wherein the step of removing the light blocking device from the measuring instrument leaves a shield layer of the removable calibration target attached to the output end of the measuring instrument.

* * * * *